(12) United States Patent
Ha et al.

(10) Patent No.: US 9,783,639 B2
(45) Date of Patent: Oct. 10, 2017

(54) DIAMINE COMPOUND, AND POLYAMIC ACID AND POLYIMIDE USING THE SAME

(71) Applicant: Pusan National University Industry-University Cooperation Foundation, Busan (KR)

(72) Inventors: Chang-Sik Ha, Busan (KR); Tapaswi Pradip Kumar, Busan (KR); Myeon Cheon Choi, Busan (KR); Keuk Min Jeong, Jinju-si (KR)

(73) Assignee: Pusan National University Industry-University Cooperation Foundation, Busan (KR)

( * ) Notice: Subject to any disclaimer, the term of this patent is extended or adjusted under 35 U.S.C. 154(b) by 0 days.

(21) Appl. No.: 14/958,010

(22) Filed: Dec. 3, 2015

(65) Prior Publication Data

US 2017/0058082 A1   Mar. 2, 2017

(30) Foreign Application Priority Data

Aug. 27, 2015 (KR) .......................... 10-2015-0121147

(51) Int. Cl.
*C08G 73/10* (2006.01)
*C07C 323/37* (2006.01)
*C07C 319/20* (2006.01)
*C08L 79/08* (2006.01)

(52) U.S. Cl.
CPC ........ *C08G 73/1039* (2013.01); *C07C 319/20* (2013.01); *C07C 323/37* (2013.01); *C08G 73/1067* (2013.01); *C08G 73/10* (2013.01); *C08L 79/08* (2013.01)

(58) Field of Classification Search
CPC . C08L 79/08; C08G 73/10; C08G 2261/3162; C08G 73/1071; C08G 73/1082; C08G 73/1039; C08G 73/1067; C07C 323/37
See application file for complete search history.

(56) References Cited

FOREIGN PATENT DOCUMENTS

| JP | 2006193434 A | 7/2006 |
|---|---|---|
| KR | 1020080055544 A | 6/2008 |
| KR | 1020130061404 A | 6/2013 |
| KR | 1020150078618 A | 7/2015 |

OTHER PUBLICATIONS

Tapaswi et al ("Transparent Aromatic Polyimides Derived from Thiophenyl-Substituted Benzidines with High Refractive Index and Small Birefringence", Macromolecules 2015, 48, 3462-3474, Published on May 19, 2015).*
USPTO search report, published Jan. 2017.*
Fang et al., "Sulfonated polyimides: Synthesis, proton conductivity and water stability", Journal of Power Sources, 2006, pp. 4-11, vol. 159.
Tapaswi et al., "Synthesis and Characterization of Highly Transparent and Hydrophobic Fluorinated Polyimides Derived from Perfluorodecylthio Substituted Diamine Monomers", Journal of Polymer Science, Part A: Polymer Chemistry, 2015, pp. 479-488, vol. 53.

* cited by examiner

*Primary Examiner* — Gregory Listvoyb
(74) *Attorney, Agent, or Firm* — The Webb Law Firm (57) ABSTRACT

Provided are a diamine compound, a polyamic acid and polyimide using the same. The diamine monomer compound is useful for preparing a transparent polyamic acid and polyimide having a high refractive index and a low birefringence.

12 Claims, 5 Drawing Sheets

DIAMINE COMPOUND, AND POLYAMIC ACID AND POLYIMIDE USING THE SAME

CROSS-REFERENCE TO RELATED APPLICATION

This application claims priority to Korean Patent Application No. 10-2015-0121147 filed Aug. 27, 2015, the disclosure of which is hereby incorporated in its entirety by reference.

TECHNICAL FIELD

The following disclosure relates to a novel diamine compound, a polyamic acid and polyimide using the same, and more specifically, to a novel diamine monomer compound having a symmetric structure which is useful in preparing a transparent polyamic acid and polyimide having a high refractive index and a low birefringence, and polyamic acid and polyimide using the same.

BACKGROUND

A glass substrate used in a conventional flat panel display has advantages such as high heat resistance, transparency, and blocking property, but may be broken if the glass substrate is dropped, and has no flexibility and is heavy even with a thin thickness. Accordingly, various researches into a flexible display that is capable of replacing the glass substrate have been in progress. Polyimide widely used in the flexible display has been widely used not only for various electronic device fields such as an interlayer insulating film for a semiconductor, a buffer coat, a substrate for a flexible printed circuit, a liquid crystal alignment film, an electrical insulating material, a substrate for a flexible display, and the like, but also for high-tech with high heat-resistant materials such as automotive materials, aerospace materials, and the like, due to excellent properties such as mechanical properties, heat resistance, chemical resistance, electrical insulation, and the like.

In general, colorless transparent polyimide is usable as materials for manufacturing transparent and highly heat resistant coating films or films in various electronic device fields such as an electrode insulating film, a transparent protective film, a hard coating layer of a touch panel in a liquid crystal display field, a hard coating layer on a transparent flexible substrate, a transparent film material, and the like. As the related art documents preparing the polyimide, Korean Patent Laid-Open Publication No. 10-2008-055544 (Jun. 19, 2008) discloses a colorless transparent polyimide resin including 4,4'-(4,4'-isopropylidenediphenoxy)bis(phthalic anhydride) (HBDA) as aromatic dianhydride and including either of diamine and fluorine-containing diamine having flexible groups as aromatic diamine or compounds of two or more thereof, and Korean Patent Laid-Open Publication No. 10-2013-0061404 (Jun. 11, 2013) discloses a diamine compound in which aromatic diamine is linked to an aryl group through linking groups consisting of an ester group or an amide group, and preparation of polyamic acid and polyimide prepared by using the diamine compound. Further, Korean Patent Laid-Open Publication No. 10-2015-0078618 (Jul. 8, 2015) discloses a diamine compound in which two aromatic diamines are linked to alkylene through ring linking groups, and preparation of polyamic acid and polyimide prepared by using the same.

The polyimide prepared by using the diamine compound disclosed as the related art has a high birefringence due to an aromatic ring structure with high density, and accordingly, there is limitation in replacing a glass substrate for LCD with a polyimide substrate. As a method for realizing a low birefringence of polyimide, there is a method of preparing polyamic acid by using a fluorine-based compound or an aliphatic compound, and then preparing polyimide by thermal cyclization of the polyamic acid. However, the method of using the fluorine-based compound and the aliphatic compound may improve birefringence, but remarkably deteriorates heat resistance, such that the method is required to be improved.

Therefore, the present applicants found that highly heat-resistant polyimide is capable of being prepared by using a novel diamine monomer compound obtained by introducing aromatic ring substituents including electron-accepting heteroatoms and halogen atoms into electron-donating biphenyl diamine to minimize intramolecular charge mobility, thereby maximizing transparency of the polyimide prepared by using the same and implementing a high refractive index and a low birefringence at the same time, and completed the present invention.

RELATED ART DOCUMENT (Patent Document 1) Korean Patent Laid-Open Publication No. 10-2008-055544 (Jun. 19, 2008)

(Patent Document 2) Korean Patent Laid-Open Publication No. 10-2013-0061404 (Jun. 11, 2013)

(Patent Document 3) Korean Patent Laid-Open Publication No. 10-2015-0078618 (Jul. 8, 2015)

SUMMARY

An embodiment of the present invention is directed to providing a novel diamine monomer compound capable of forming a highly heat-resistant polyimide film having a high refractive index and a low birefringence, and a preparation method thereof.

Another embodiment of the present invention is directed to providing polyamic acid and polyimide using the diamine monomer compound, and a preparation method thereof.

In one general aspect, there is provided a diamine monomer compound represented by Chemical Formula 1 below:

[Chemical Formula 1]

in Chemical Formula 1, $L_1$ is each independently O, S or Se;

$L_2$ is each independently (C6-30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri (C6-C30)arylsilyl, nitro and hydroxy; and

$X_1$ is each independently halogen.

In another general aspect, there is provided a preparation method of a diamine monomer compound represented by Chemical Formula 1 below, the preparation method including: preparing the compound represented by Chemical Formula 1 below through benzidine rearrangement of a compound represented by Chemical Formula 6 below:

[Chemical Formula 1]

[Chemical Formula 6]

in Chemical Formulas 1 and 6, $L_1$ is each independently O, S or Se;

$L_2$ is each independently (C6-C30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri (C6-C30)arylsilyl, nitro and hydroxy; and $X_1$ is halogen.

In another general aspect, there is provided a polymer material obtained by a polymerization reaction using the diamine monomer compound as described above.

In another general aspect, there is provided a polyamic acid represented by Chemical Formula 9 below obtained by a polymerization reaction between the diamine monomer compound as described above and a tetracarboxylic acid represented by Chemical Formula 7 below or dianhydride represented by Chemical Formula 8 below, using a monomer:

[Chemical Formula 7]

[Chemical Formula 8]

[Chemical Formula 9]

in Chemical Formulas 7 to 9, $L_1$ is each independently O, S or Se;

$L_2$ is each independently (C6-C30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri (C6-C30)arylsilyl, nitro and hydroxy;

A is (C3-C30)cycloalkyl, (C3-C30)heterocycloalkyl, (C6-C30)aryl or (C3-C30)heteroaryl, wherein heterocycloalkyl and heteroaryl each independently include at least one heteroatom selected from the group consisting of =B—, =N—, —O—, —S—, —P(=O)—, —Si— and P;

n is an integer of 5 to 100,000; and $X_1$ is halogen.

In another general aspect, there is provided a polyimide obtained by a cyclization reaction of the polyamic acid as described above.

DETAILED DESCRIPTION OF EMBODIMENTS

Hereinafter, a novel diamine monomer compound having a symmetric structure which is useful in manufacturing a transparent polyimide film simultaneously having a high refractive index and a low birefringence, and polyamic acid and polyimide using the same will be described. Meanwhile, unless technical and scientific terms used herein are defined otherwise, they have meanings understood by those skilled in the art to which the present invention pertains. Known functions and components will be omitted so as not to obscure the description of the present invention with unnecessary detail.

The diamine monomer compound according to the present invention may have high atomic polarization of a molecular structure by including atoms having large volume such as electron-accepting heteroatoms, halogen atoms, and the like, in electron-donating biphenyl diamine, such that the polyimide prepared therefrom may minimize charge transfer and interaction of polyimide chains, thereby reducing coloring of the polyimide and implementing more improved refractive index.

In addition, the diamine monomer compound represented by Chemical Formula 1 below according to the present invention may form large open volume in a main chain of polyimide by introducing aromatic substituents including atoms having large volume:

[Chemical Formula 1]

in Chemical Formula 1, $L_1$ is each independently O, S or Se;

$L_2$ is each independently (C6-C30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri(C1-C30)alkylsilyl, di(C1-C30)alkyl(C6-C30)arylsilyl, tri(C6-C30)arylsilyl, nitro and hydroxy; and $X_1$ is each independently halogen.

Term: "arylene" used herein, which is an organic radical derived from aromatic hydrocarbon due to removal of two hydrogen, includes a single ring system or a fused ring system suitably including 4 to 7 ring atoms, preferably, 5 or 6 ring atoms in each ring, and even includes a form in which a plurality of aryls are connected to each other by a single bond. Specific examples of the arylene may include phenylene, naphthylene, biphenylene, anthrylene, indenylene, fluorenylene, phenanthrylene, triphenylene, pyrenylene, and the like, but the present invention is not limited thereto.

Term: "heteroarylene" used herein, which is an organic radical derived from aromatic hydrocarbon due to removal of two hydrogen, may be a monocyclic or polycyclic aromatic hydrocarbon radical including 3 to 8 ring atoms including at least one heteroatom selected from B, N, O, S, P(=O), Si and P, and includes a single ring system or a fused ring system suitably including 3 to 7 ring atoms, preferably, 5 or 6 ring atoms in each ring, and even includes a form in which a plurality of heteroaryls are connected to each other by a single bond. Specific examples include monocyclic heteroarylenes such as furylene, thiophenylene, pyrrolylene, pyranylene, imidazolylene, pyrazolylene, thiazolylene, thiadiazolylene, isothiazolylene, isoxazolylene, oxazolylene, oxadiazolylene, triazinylene, tetrazinylene, triazolylene, tetrazolylene, furazanylene, pyridylene, pyrazinylene, pyrimidinylene, pyridazinylene, and the like; and polycyclic heteroarylenes such as benzofuranylene, benzothiophenylene, isobenzofuranylene, benzoimidazolylene, benzothiazolylene, benzoisothiazolylene, benzoisoxazolylene, benzooxazolylene, isoindolylene, indolylene, indazolylene, benzo-thiadiazolylene, quinolylene, isoquinolylene, cinnolinylene, quinazolinylene, quinolizinylene, quinoxalinylene, carbazolylene, phenanthridinylene, benzodioxolylene, and the like, but the present invention is not limited thereto.

Further, term: "alkyl", "alkoxy" and substituents including other "alkyl" portions used herein, includes both of linear and branched forms, and term: "halogen" means fluorine (F), chlorine (Cl), bromine (Br) or iodine (I), preferably, fluorine or chlorine.

In the diamine monomer compound according to an exemplary embodiment of the present invention, in order to have high atomic refraction, the $L_1$ may be each independently S or Se, and in order to have excellent physical properties and a high refractive index, $L_2$ may be each independently selected from the group consisting of phenylene, naphthylene, biphenylene, terphenylene, anthrylene, indenylene, fluorenylene, phenanthrylene, triphenylenylene, pyrenylene, furylene, thiophenylene, pyrrolylene, pyranylene, imidazolylene, pyrazolylene, thiazolylene, thiadiazolylene, isothiazolylene, triazinylene, tetrazinylene, triazolylene, tetrazolylene, furazanylene, pyridinylene, pyrazinylene, benzofuranylene, benzothiophenylene, and the like, but the present invention is not limited thereto.

In detail, the diamine monomer compound according to the present invention may be represented by Chemical Formula 2 below, which is prepared by introducing substituents including atoms having large volume such as heteroatoms and halogen atoms at a meta position of a symmetric structure on a non-coplane to biphenyl diamine to be capable of providing strong rigidity to a main chain of polyimide prepared by using the diamine monomer compound:

[Chemical Formula 2]

in Chemical Formula 2, $L_1$ is each independently O, S or Se; and

$X_1$ is each independently halogen.

In detail, the diamine monomer compound according to the present invention simultaneously has a high refractive index and a low birefringence and has aromatic ring substituents including atoms having large volume at a meta position of biphenyl diamine, and accordingly, the diamine monomer compound may be selected from the following structure in order to maintain rigidity of the main chain of the polymer, but the present invention is not limited thereto:

The diamine monomer compound according to the present invention may be prepared by various synthetic methods. However, the diamine monomer compound may be prepared by a preparation method of a diamine monomer compound represented by Chemical Formula 1 below, the preparation method including: preparing the compound represented by Chemical Formula 1 through benzidine rearrangement of a compound represented by Chemical Formula 6 below in order to have a high reaction yield and mild reaction conditions:

[Chemical Formula 1]

[Chemical Formula 6]

in Chemical Formulas 1 and 6,

$L_1$ is each independently O, S or Se;

$L_2$ is each independently (C6-C30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri(C1-C30)alkylsilyl, di(C1-C30)alkyl(C6-C30)arylsilyl, tri(C6-C30)arylsilyl, nitro and hydroxy; and

$X_1$ is halogen.

In addition, the compound represented by Chemical Formula 6 above may be prepared by the following steps: preparing a compound represented by Chemical Formula 5 below by reacting a compound represented by Chemical Formula 3 below with a compound represented by Chemical Formula 4 below; and preparing the compound represented by Chemical Formula 6 below by forming diazene from the compound represented by Chemical Formula 5 in the presence of zinc and then converting the diazene into diazane, but the present invention is not limited thereto:

[Chemical Formula 1]

[Chemical Formula 3]

[Chemical Formula 4]

[Chemical Formula 5]

-continued

[Chemical Formula 6]

in Chemical Formulas 1, 2 to 6, $L_1$ is each independently O, S or Se;

$L_2$ is each independently (C6-C30)arylene or (C6-C30) heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30) alkyl, halo(C1-C30)alkyl, halogen, (C3-C30)cycloalkyl, (C1-C30)alkoxy, (C6-C30)aryloxy, (C6-C30)aryl, (C6-C30) ar(C1-C30)alkyl, (C1-C30)alkyl(C6-C30)aryl, (C3-C30) heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri (C6-C30)arylsilyl, nitro and hydroxy; and $X_1$ and $X_a$ are each independently halogen.

In the preparation method according to an exemplary embodiment of the present invention, in the diamine monomer compound capable of preparing polyimide having a high refractive index and a low birefringence and also having high solubility and transparency without deteriorating heat resistance, $L_1$ may be each independently S or Se, and $L_2$ may be each independently selected from the group consisting of phenylene, naphthylene, biphenylene, terphenylene, anthrylene, indenylene, fluorenylene, phenanthrylene, triphenylenylene, pyrenylene, furylene, thiophenylene, pyrrolylene, pyranylene, imidazolylene, pyrazolylene, thiazolylene, thiadiazolylene, isothiazolylene, triazinylene, tetrazinylene, triazolylene, tetrazolylene, furazanylene, pyridinylene, pyrazinylene, benzofuranylene, benzothiophenylene, and the like, but the present invention is not limited thereto.

The preparation method according to an exemplary embodiment of the present invention may be performed in the presence of general solvents. Non-limiting examples of the solvent may include at least one solvent selected from the group consisting of C1-C4 alcohol, N-methyl-2-pyrrolidone (NMP), N,N-dimethylacetamide (DMAc), dimethylformamide (DMF), m-cresol, dimethyl sulfoxide (DMSO), acetone, diethyl acetate, and the like, but the present invention is not limited thereto.

The present invention provides a polymer material obtained by a polymerization reaction using the diamine monomer compound represented by Chemical Formula 1 above. Here, the polymer material may be a polyamic acid obtained by a polymerization reaction between the diamine monomer compound according to the present invention and a tetracarboxylic acid or dianhydride or a polyimide obtained by a cyclization reaction of the polyamic acid.

The polyamic acid according to an exemplary embodiment of the present invention may be obtained by a polymerization reaction between the diamine monomer compound represented by Chemical Formula 1 and the tetracarboxylic acid represented by Chemical Formula 7 below or the dianhydride represented by Chemical Formula 8 below, and the polyamic acid may be represented by Chemical Formula 9 below:

[Chemical Formula 1]

[Chemical Formula 7]

[Chemical Formula 8]

[Chemical Formula 9]

in Chemical Formulas 1, 7 to 9, $L_1$ is each independently O, S or Se;

$L_2$ is each independently (C6-C30)arylene or (C6-C30) heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30) alkyl, halo(C1-C30)alkyl, halogen, (C3-C30)cycloalkyl, (C1-C30)alkoxy, (C6-C30)aryloxy, (C6-C30)aryl, (C6-C30) ar(C1-C30)alkyl, (C1-C30)alkyl(C6-C30)aryl, (C3-C30) heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri (C6-C30)arylsilyl, nitro and hydroxy;

A is (C3-C30)cycloalkyl, (C3-C30)heterocycloalkyl, (C6-C30)aryl or (C3-C30)heteroaryl, wherein heterocycloalkyl and heteroaryl each independently include at least one heteroatom selected from the group consisting of =B—, =N—, —O—, —S—, —P(=O)—, —Si— and P;

n is an integer of 5 to 100,000; and $X_1$ is halogen.

The n of the polyamic acid according to an exemplary embodiment of the present invention is preferably an integer of 10 to 50,000, and more preferably, an integer of 100 to 10,000.

A of the tetracarboxylic acid or the dianhydride according to an exemplary embodiment of the present invention may be selected from structures below, but the present invention is not limited thereto:

In addition, the polyamic acid according to an exemplary embodiment of the present invention may be prepared by using the tetracarboxylic acid or the dianhydride in an amount of 1 to 200 moles, preferably, 10 to 150 moles, and more preferably, 50 to 100 moles, based on 1 mole of the diamine monomer compound. Here, the polyamic acid may be prepared in the presence of a polar solvent at 0 to 300° C., and may be prepared under mild conditions such as room temperature (20° C.) to 50° C. due to high reactivity of the diamine monomer compound according to the present invention.

The present invention provides a polyimide represented by Chemical Formula 10 below, obtained by a cyclization reaction of the polyamic acid represented by Chemical Formula 9. Here, the cyclization reaction of the polyamic acid may be performed under general cyclization conditions. Here, in order to effectively perform an imidization reaction which is the cyclization reaction, a catalytic amount of a dehydrating-cyclization agent, an imidization catalyst, or the like, may be further added thereto, but the present invention is not limited to the above-described materials.

[Chemical Formula 10]

in Chemical Formula 10, $L_1$ is each independently O, S or Se;

$L_2$ is each independently (C6-C30)arylene or (C6-C30) heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30) alkyl, halo(C1-C30)alkyl, halogen, (C3-C30)cycloalkyl, (C1-C30)alkoxy, (C6-C30)aryloxy, (C6-C30)aryl, (C6-C30) ar(C1-C30)alkyl, (C1-C30)alkyl(C6-C30)aryl, (C3-C30) heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri (C6-C30)arylsilyl, nitro and hydroxy;

A is (C3-C30)cycloalkyl, (C3-C30)heterocycloalkyl, (C6-C30)aryl or (C3-C30)heteroaryl, wherein heterocycloalkyl and heteroaryl each independently include at least one heteroatom selected from the group consisting of =B—, =N—, —O—, —S—, —P(=O)—, —Si— and P;

n is an integer of 5 to 100,000; and $X_1$ is halogen.

In addition, the present invention is capable of forming a polyimide film by dissolving the polyamic acid or polyimide in a solvent and coating the polyamic acid or polyimide on a substrate, followed by heat treatment. Here, the solvent is not limited as long as it is a solvent which is generally used in the art. Preferably, the solvent may be at least one polar solvent selected from the group consisting of N-methyl-2-pyrrolidone (NMP), N,N-dimethylacetamide (DMAc), dimethylformamide (DMF), m-cresol, dimethyl sulfoxide (DMSO), acetone, diethyl acetate, and the like. However, the present invention is not limited to the above-described solvent.

The coating according to an exemplary embodiment of the present invention may be performed by impregnation, casting coating, or the like, and may be performed at 60 to 400° C. for 30 minutes to 48 hours. In addition, it is preferred that the heat treatment is sequentially performed from a low temperature to a high temperature into two or more stages. The most preferably, the heat treatment is performed at 60° C. to 100° C. for 1 hour to 24 hours, at 110° C. to 150° C. for 30 minutes to 5 hours, at 160° C. to 200° C. for 30 minutes to 5 hours, at 210° C. to 250° C. for 30 minutes to 2 hours, and at 260° C. to 300° C. for 30 minutes to 2 hours.

Hereinafter, the present invention will be described in detail by the following Examples. However, the following Examples of the present invention have been described to help the understanding of the present invention. Therefore, the scope of the present invention is not limited to these Examples.

Example 1

Synthesis of 2,2'-Bis(4-chlorothiophenyl)benzidine (BTPB)

BTPB

Step 1. Synthesis of (4-Chlorophenyl)(3-nitrophenyl)sulfane (2)

200 ml of dried DMF was added to a 500 ml round bottom flask under nitrogen atmosphere. 4-Chlorothiophenol (21.69 g, 150 mmol), 1-iodo-3-nitrobenzene (37.35 g, 150 mmol), $K_2CO_3$ (41.4 g, 300 mmol), CuI (4.29 g, 22.5 mmol), and PEG-400 (5 mL) were added thereto and reacted at 120° C. for 12 hours. Then, the mixture was cooled to room temperature (20° C.) and a wine red colored solution was filtered. The filtrate was concentrated on a rotary evaporator, and 400 ml of cold ice water was slowly poured to filter white precipitate. The obtained product was washed with cold water three times, and vacuum-dried at 60° C. for 12 hours, to obtain an off-white target compound (36.7 g, 92%).

Melting point (mp); 63-64° C.

$^1$H-NMR (400 MHz, DMSO-$d_6$): δ 8.11 (bd, J=8.0 Hz, 1H, Ph-H), 7.98 (t, J=2.0 Hz, 1H, Ph-H), 7.70 (d, J=8.0 Hz, 1H, Ph-H), 7.65 (t, J=8.0 Hz, 1H, Ph-H), 7.55-7.50 (m, 4H, Ph-H)

$^{13}$C-NMR (100 MHz, DMSO-$d_6$): δ 148.4, 139.9, 134.8, 133.8, 132.9, 130.7, 130.5, 129.9, 123.0, 122.6

Anal. calcd. for $C_{12}H_8ClNO_2S$: C, 54.24; H, 3.03; N, 5.27. found: C, 54.12; H, 3.10; N, 5.32.

FT-IR (KBr, cm$^{-1}$): 1518, 1347, 1087, 821, 725.

Step 2: Synthesis of Diazene Compound (3)

(4-Chlorophenyl) 3-nitrophenyl)sulfane (2) (26.5 g, 100 mmol) was dispersed in ethanol (200 ml), and the dispersion was poured into a sodium hydroxide solution (20 ml) containing sodium hydroxide (20 g, 500 mmol). Zinc powder (18 g, 275 mmol) was slowly added to the mixture and refluxed while stirring for one day. The hot reaction mixture was washed with ethanol and filtered. The filtrate was added to cold water (500 ml) and stirred to obtain a precipitate. The precipitate was dried at 40° C. for 24 hours in a vacuum oven to obtain an orange yellow target compound, and directly used in the next step without further purification (19.6 g, 84%).

Step 3: Synthesis of Diazene Compound (4)

Zinc powder (2.62 g, 40 mmol) was slowly added to a diazene compound (3) (18.7 g, 40 mmol) which is not dissolved in acetone (100 ml). NH$_4$Cl (40 ml) was slowly further added thereto. The mixture was reacted at room temperature for 3 hours and extracted with chloroform. One drop of 10% ammonia solution was added to the extracted solution to obtain a solid, and the obtained solid was filtered to obtain a light yellow solid (17.7 g, 94%).

$^1$H-NMR (400 MHz, DMSO-$d_6$): δ 8.31 (s, 2H, —NH), 7.81 (d, J=7.5 Hz, 4H, Ph-H), 7.76 (br, d, J=3.0 Hz, 2H, Ph-H), 7.62 (t, J=6.0 Hz, 2H, Ph-H), 7.48-7.41 (m, 8H, Ph-H).

FT-IR (KBr, cm$^{-1}$): 3345, 1595, 1472, 1089.

Step 4: Synthesis of Diamine Monomer Compound 2,2'-Bis(4-chlorothiophenyl)benzidine (BTPB)

A diazane solution was prepared by dissolving the diazane compound (4) (16.9 g, 36 mmol) in dried ethanol (200 ml) under nitrogen atmosphere. Ethanol-hydrochloric acid (1:1) (80 ml) was added to ice water and cooled to 0° C., and then was added to the diazane solution for 2 hours. After the addition was completed, ice bath was removed, and stirred at room temperature for 6 hours to obtain a white solid precipitate. The precipitate was filtered and washed with ethanol several times, and the obtained precipitate was dissolved in water (100 ml). 10% aqueous sodium hydroxide solution was added thereto, and organic materials were extracted with DCM. The extracted materials with DCM were evaporated and dried to obtain a white solid. The white solid was re-crystallized with solution (EtOAc:hexane=1:1) (12.2 g, 72.0%).

Melting point (mp); 168-169° C.

$^1$H-NMR (400 MHz, DMSO-d6): δ 7.20 (bs, 4H, Ph-H), 6.98 (d, J=6.4 Hz, 1H, Ph-H), 6.55 (dd, J=6.4 Hz 2.0 Hz, 1H, Ph-H), 6.48 (d, J=2.0 Hz, 1H, Ph-H), 3.63 (s, 4H, NH$_2$)

$^{13}$C-NMR (100 MHz, DMSO-d6): δ 146.6, 136.7, 134.5, 133.1, 133.0, 132.9, 132.1, 131.9, 131.6, 129.2, 129.1, 129.0, 116.8, 116.7, 113.8, 113.7

Anal. calcd. for C$_{24}$H$_{18}$Cl$_2$N$_2$S$_2$: C, 61.40; H, 3.86; N, 5.97.

found: C, 61.27; H, 3.91; N, 6.05.

FT-IR (KBr, cm$^{-1}$): 3327, 3078, 3020, 1600, 1470, 1277, 1225, 1089, 1011, 824

Crystal data: 0.22×0.13×0.07 mm, C24H18C12N2S2, light yellow, f$_w$=469.42; Orthorhombic, P2(1)2(1)2(1); a=9.3298(4) Å, b=12.8039(6) Å, c=18.0035(8) Å, α=β=γ=90°; V=2150.66(17) Å$^3$, Z=4; T=200(2) K, R indices [I>2sigma(I)]: R1=0.0510, wR2=0.0947; R indices (all data): R1=0.0918, wR2=0.1583; GOF=1.136.

Figure 1:
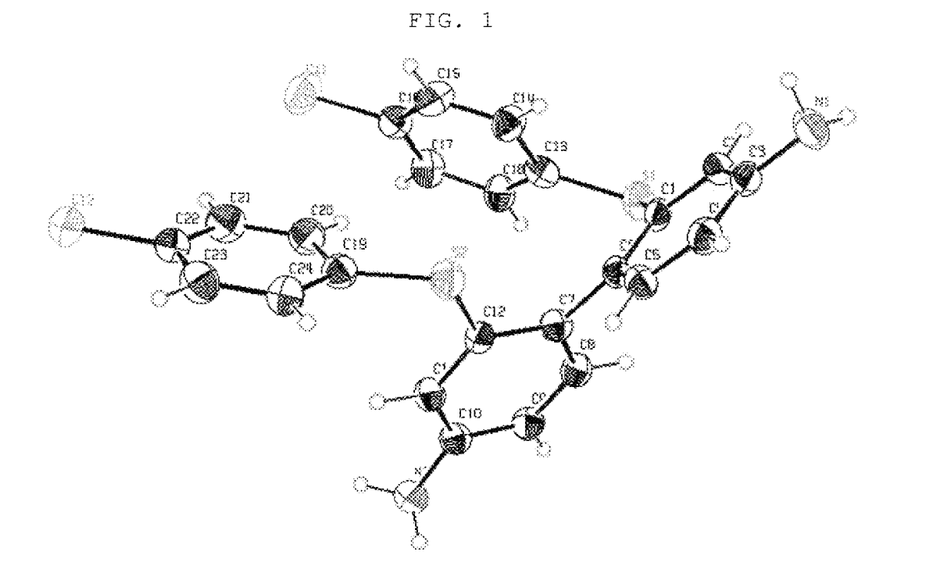
FIG. 1 is an oak ridge thermal ellipsoid plot (ORTEP) diagram illustrating a single crystal of a diamine monomer compound prepared by Example 1 of the present invention.
Figure 2:
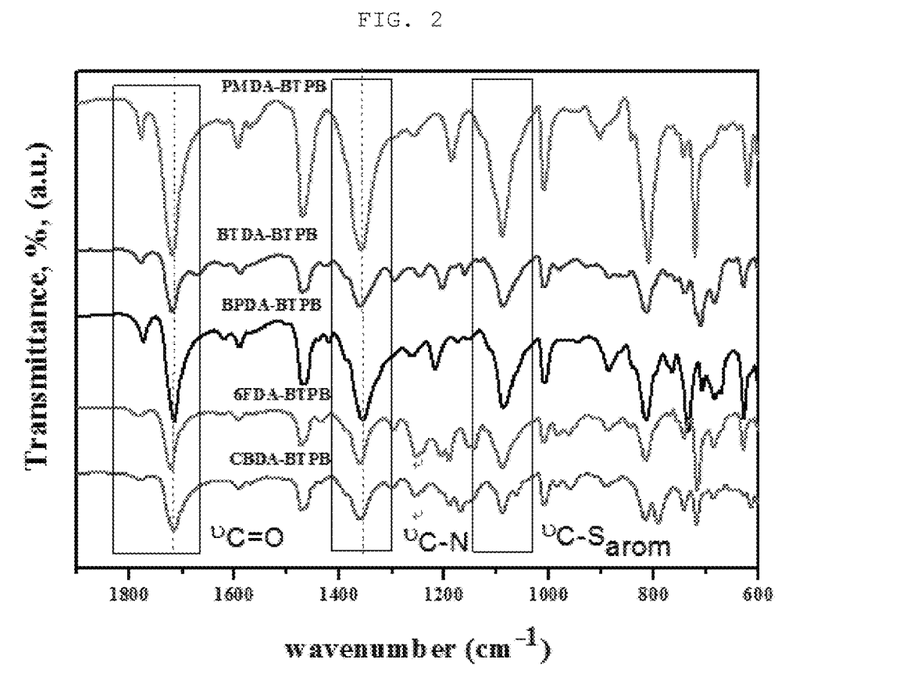
FIG. 2 is a Fourier-transform infrared spectroscopy (FTIR) spectrum of polyimides prepared by Examples 2 to 6 of the present invention.
Figure 3:
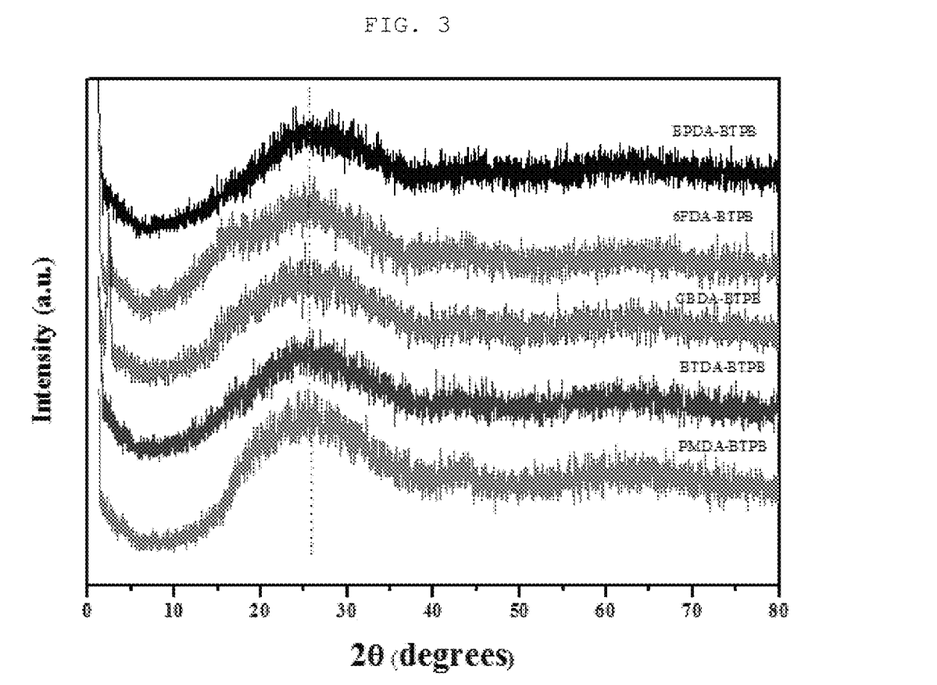
FIG. 3 illustrates analysis results of wide angle x-ray diffractograms (waxd) of polyimides prepared by Examples 2 to 6 of the present invention.
Figure 4:
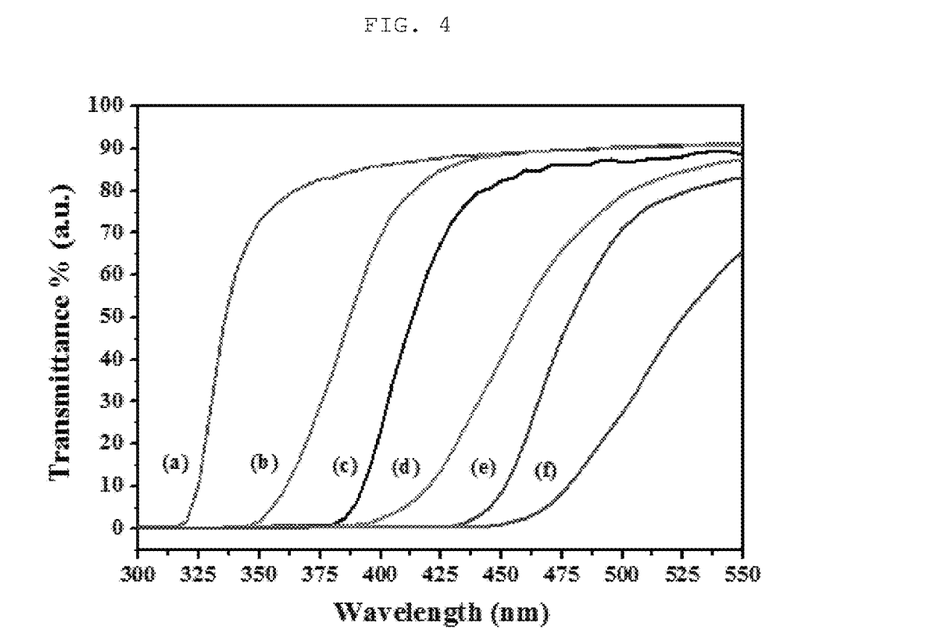
FIG. 4 illustrates optical transmission spectrums ((a) Example 3—CBDA-BTPB; (b) Example 2—6FDA-BTPB; (c) Example 4—BPDA-BTPB; (d) Example 5—PMDA-BTPB; (e) Example 6—BTDA-BTPB; (f) PMDA-ODA) of polyimides prepared by Examples 2 to 6 of the present invention.
Figure 5:
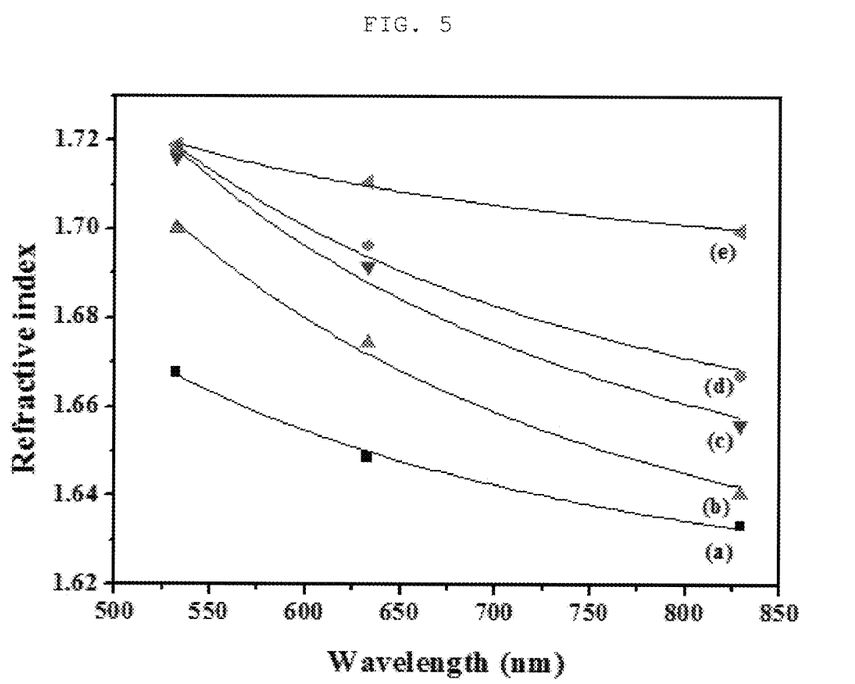
FIG. 5 illustrates analysis results of wavelength dispersion of polyimides prepared by Examples 2 to 6 of the present invention.
Figure 6:
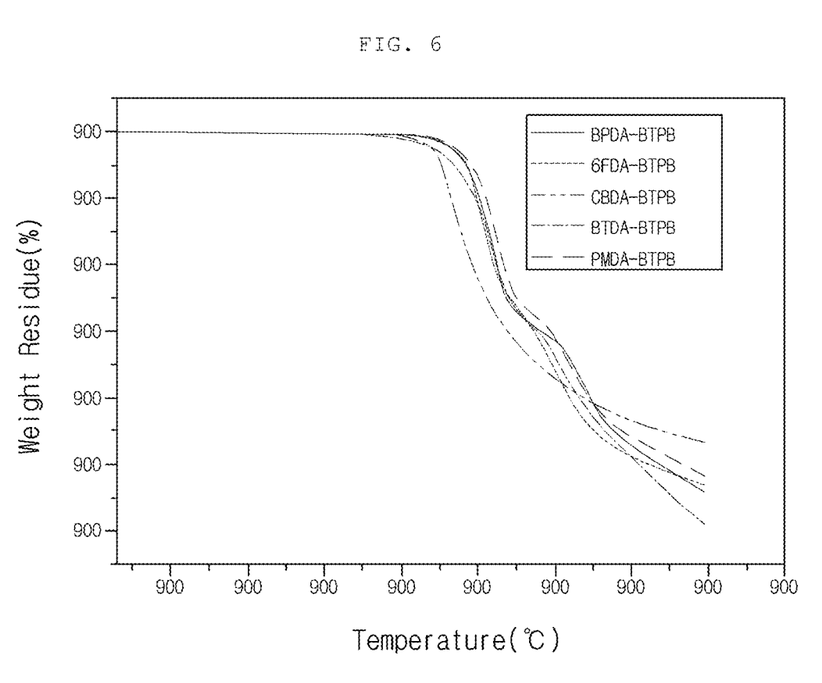
FIG. 6 is a thermogravimetric analysis (TGA) graph illustrating thermal properties of polyimides prepared by Examples 2 to 6 of the present invention.
Figure 7:
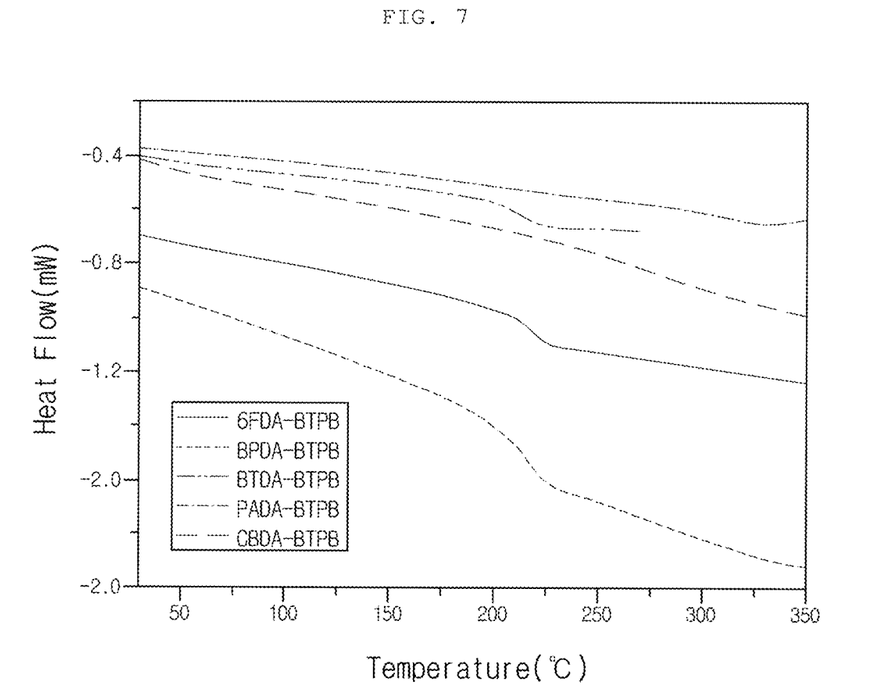
FIG. 7 is a differential calorimetry (DSC) graph illustrating thermal properties of polyimides prepared by Examples 2 to 6 of the present invention.

It may be appreciated from an oak ridge thermal ellipsoid plot (ORTEP) diagram of a single crystal of the diamine monomer compound prepared by Example 1 above that a torsion angle (plane 1: C7-C12 and plane 2: C6-C5) between phenyl rings of two central nitrogen bonds is 55.07°, and a torsion angle (plane 3: C1-S1 and plane 4: C12-S2) between two C—S bonds is 130.24°, and a torsion angle (plane 5: C24-C19 and C13-C14) between 1,4-disubstituted phenyl rings is 49.03°.

That is, it may be appreciated that the phenyl rings of the diamine monomer compound are 2,2-disubstituted in non-coplanar forms.

As illustrated in FIG. 1, the diamine monomer compound (BTPB) prepared by Example 1 above has a non-coplanar twist bar form. The form may hinder close packing of polymer chains to enhance solubility in forming polyimide. Meanwhile, the non-coplanar structure may effectively reduce charge transfer and interaction in molecules and among molecules to increase optical transparency of the polyimide film manufactured by using the non-coplanar structure. In addition, a refractive index of BTPB-based polyimide may be effectively increased by heteroatoms such as sulfur, chlorine, and the like, which are present in the substituents of BTPB.

Example 2

The diamine monomer compound (BTPB) (1 mmol, 0.469 g) prepared by Example 1 and 4,4'-(hexafluoroisopropylidene)diphthalic anhydride (6FDA) (1 mmol, 0.444 g) were dissolved in NMP (2.13 g) under nitrogen atmosphere and stirred at room temperature for 48 hours to prepare a polyamic acid (3.04 g, 30%).

The polyamic acid (20 g) prepared by the above-described method was dissolved in NMP (80 g), followed by spin-coating on a glass substrate and loading nitrogen under imidization crosslinking conditions, and dried at 80° C. for 8 hours, at 150° C. for 2 hours, at 200° C. for 2 hours, at 250° C. for 1 hour and at 300° C. for 1 hour. Then, the glass substrate was added to water to obtain a polyimide film.

Example 3

A polyimide film was obtained by the same method as Example 2 except for using cyclobutane-1,2,3,4-tetracarboxylic dianhydride (CBDA) (1 mmol, 0.196 g) instead of using 4,4'-(hexafluoroisopropylidene)diphthalic anhydride (6FDA).

Example 4

A polyimide film was obtained by the same method as Example 2 except for using 3,3',4,4'-biphenyltetracarboxyic dianhydride (BPDA) (1 mmol, 0.294 g) instead of using 4,4'-(hexafluoroisopropylidene)diphthalic anhydride (6FDA).

Example 5

A polyimide film was obtained by the same method as Example 2 except for using pyromellitic dianhydride (PMDA) (1 mmol, 0.218 g) instead of using 4,4'-(hexafluoroisopropylidene)diphthalic anhydride (6FDA).

Example 6

A polyimide film was obtained by the same method as Example 2 except for using 3,3',4,4'-benzophenone-3,3',4,4'-tetracarboxylic dianhydride (BTDA) (1 mmol, 0.322 g) instead of using 4,4'-(hexafluoroisopropylidene)diphthalic anhydride (6FDA)

A refractive index (n$_{TE}$, n$_{TM}$) and a birefringence (Δn) of the polyimide films manufactured by the above-described method were measured at 633 nm by the following methods, and the results thereof were shown in Table 1 below, and physical and chemical properties of the polyimide films were measured, and the results thereof were shown in Table 2 below and FIGS. 2 to 7.

Method of Measuring Refractive Index

A refractive index in a horizontal direction, a refractive index in a vertical direction, and an average refractive index were measured by using an Abbe refractometer (Atago Co., Ltd.).

Method of Measuring Birefringence

The birefringence was measured at 633 nm three times by a refringence analyzer (Prism Coupler, Sairon SPA 4000), and an average thereof was determined as the birefringence.

In addition, the viscosity of each polyamic acid prepared by Examples 2 to 6 was measured by Oswald viscometer at 25° C. As a result, it was confirmed that the viscosities were 1.25, 0.98, 1.18, 1.22, and 1.20 dL/g, and that characteristic peaks of the polyamic acid were 1781-1774 (C=O, asymmetric), 1720-1716 (C=O, symmetric), 1362-1354 (C—N) and 1090-1084 (C—S$_{aromatic}$), respectively, by FT-IR (KBr, cm$^{-1}$).

Table 1 below shows results of refractive indices (n$_{TE}$, n$_{TM}$) and birefringences (Δn) at 633 nm of the polyimides prepared by Examples 2 to 6, wherein n$_{TE}$ indicates refractive indices in a horizontal direction, n$_{TM}$ indicates refractive indices in a vertical direction, n$_{av}$ indicates average refractive indices, Δn indicates birefringences, n$_\infty$ indicates refractive indices at infinite wavelength, D indicates coefficients of wavelength dispersion, V indicates Abbe numbers, and λ$_{cutoff}$ indicates measurement wavelength regions.

TABLE 1

| Example | nTE | nTM | $n_{av}$ | $\Delta n$ | $n\infty$ | D ($10^{-3}$) | V | $\lambda_{cutoff}$ (nm) |
|---|---|---|---|---|---|---|---|---|
| 2 | 1.6489 | 1.6485 | 1.6487 | 0.0004 | 1.6087 | 16.55 | 20.78 | 358 |
| 3 | 1.6961 | 1.6973 | 1.6963 | 0.0012 | 1.6334 | 24.16 | 15.26 | 445 |
| 4 | 1.6737 | 1.6759 | 1.6744 | 0.0022 | 1.6005 | 28.59 | 12.51 | 322 |
| 5 | 1.6911 | 1.6927 | 1.6916 | 0.0016 | 1.6156 | 29.02 | 12.63 | 414 |
| 6 | 1.7107 | 1.7103 | 1.7106 | 0.0004 | 1.6868 | 9.19 | 40.53 | 387 |

Table 2 below shows color at a thickness of 20 μm, glass transition temperature, each temperature at 5% weight loss and 10% weight loss, a residual weight ratio at 800° C. ($R_{w800}$) and a coefficient of thermal expansion (CTE), of each polyimide prepared by Examples 2 to 6.

TABLE 2

| Example | Film[a] | $T_g$ (° C.)[b] DSC | $T_g$ (° C.)[b] DMA | $T_d^5$ (° C.)[c] | $T_d^{10}$ (° C.)[c] | $R_{w800}$ (%)[d] | CTE (ppm/K) |
|---|---|---|---|---|---|---|---|
| 2 | colorless | 228 | 244 | 487 | 501 | 47 | 60.8 |
| 6 | yellow | 219 | 239 | 469 | 495 | 41 | 63.0 |
| 3 | colorless | — | 263 | 453 | 468 | 53 | 35.9 |
| 5 | pale yellow | 328 | 306 | 490 | 509 | 48 | 10.0 |
| 4 | almost colorless | 225 | 243 | 484 | 499 | 46 | 39.7 |

[a]Color at the thickness of ~20 μm,
[b]Tg: glass transition temperature,
[c]Td5, Td10: temperatures at 5% and 10% weight loss, respectively;
[d]Rw800: residual weight ratio at 800° C. in nitrogen.
CTE: coefficient of thermal expansions.

As shown in Tables 1 and 2, it could be confirmed that when the polyimide film was manufactured by using the diamine monomer compound according to the present invention, a transparent polyimide film having a low birefringence and excellent heat resistant property was capable of being manufactured, the transparent polyimide film having more improved refractive index by minimizing charge transfer and interaction of polyimide chains while maintaining a rigid structure of polyimide, and including atoms having large volume such as chlorine (Cl), fluorine (F), sulfur (S), selenium (Se), and the like, to exhibit high atomic polarization phenomenon of a molecular structure.

Therefore, the diamine monomer compound according to the present invention may be effectively utilized for preparing a transparent polyamic acid and polyimide having a high refractive index and a low birefringence.

The diamine monomer compound according to the present invention may have high solubility to solvents and high atomic polarization by introducing aromatic ring substituents including electron-accepting heteroatoms and halogen atoms into electron-donating biphenyl diamine.

The polyimide prepared by using the diamine monomer compound according to the present invention may improve a refractive index by minimizing charge transfer and interaction of polyimide chains. In addition, the polyimide may have a much lower coefficient of thermal expansion (CTE) due to strong rigidity of a main chain of the polymer, and may include atoms having large volume such as chlorine (Cl), fluorine (F), sulfur (S), selenium (Se), and the like, to exhibit high atomic polarization phenomenon of a molecular structure, such that when the polyimide is manufactured into a film, excellent thermal, mechanical and optical properties may be implemented.

What is claimed is:

1. A diamine monomer compound represented by Chemical Formula 1 below:

[Chemical Formula 1]

in Chemical Formula 1, $L_1$ is each independently O, S or Se;

$L_2$ is each independently (C6-C30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri(C1-C30)alkylsilyl, di(C1-C30)alkyl(C6-C30)arylsilyl, tri(C6-C30)arylsilyl, nitro and hydroxy; and $X_1$ is each independently halogen.

2. The diamine monomer compound of claim 1, wherein $L_1$ is each independently S or Se, and $L_2$ is each independently selected from the group consisting of phenylene, naphthylene, biphenylene, terphenylene, anthrylene, indenylene, fluorenylene, phenanthrylene, triphenylenylene, pyrenylene, furylene, thiophenylene, pyrrolylene, pyranylene, imidazolylene, pyrazolylene, thiazolylene, thiadiazolylene, isothiazolylene, triazinylene, tetrazinylene, triazolylene, tetrazolylene, furazanylene, pyridinylene, pyrazinylene, benzofuranylene, and benzothiophenylene.

3. The diamine monomer compound of claim 1, wherein it is represented by Chemical Formula 2 below:

[Chemical Formula 2]

in Chemical Formula 2,
$L_1$ is each independently O, S or Se; and
$X_1$ is each independently halogen.

4. The diamine monomer compound of claim 3, wherein the diamine monomer compound is selected from the following structure:

5. A preparation method of a diamine monomer compound represented by Chemical Formula 1 below, the preparation method comprising:
preparing the compound represented by Chemical Formula 1 below through benzidine rearrangement of a compound represented by Chemical Formula 6 below:

[Chemical Formula 1]

[Chemical Formula 6]

in Chemical Formulas 1 and 6,
$L_1$ is each independently O, S or Se; and
$L_2$ is each independently (C6-C30)arylene or (C6-C30) heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri (C1-C30)alkylsilyl, di(C1-C30)alkyl(C6-C30)arylsilyl, tri(C6-C30)arylsilyl, nitro and hydroxy; and
$X_1$ is halogen.

6. The preparation method of claim 5, wherein the compound represented by Chemical Formula 6 below is prepared by the following steps:
preparing a compound represented by Chemical Formula 5 below by reacting a compound represented by Chemical Formula 3 below with a compound represented by Chemical Formula 4 below; and
preparing the compound represented by Chemical Formula 6 below by forming diazene from the compound represented by Chemical Formula 5 in the presence of zinc and then converting the diazene into diazane:

[Chemical Formula 1]

[Chemical Formula 3]

[Chemical Formula 4]

[Chemical Formula 5]

[Chemical Formula 6]

in Chemical Formulas 1, 3 to 6,
$L_1$ is each independently O, S or Se;
$L_2$ is each independently (C6-C30)arylene or (C6-C30) heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri(C1-C30)alkylsilyl, di(C1-C30)alkyl(C6-C30)arylsilyl, tri(C6-C30)arylsilyl, nitro and hydroxy; and

$X_1$ and $X_a$ are each independently halogen.

7. The preparation method of claim 5, wherein $L_1$ is each independently S or Se, and $L_2$ is each independently selected from the group consisting of phenylene, naphthylene, biphenylene, terphenylene, anthrylene, indenylene, fluorenylene, phenanthrylene, triphenylenylene, pyrenylene, furylene, thiophenylene, pyrrolylene, pyranylene, imidazolylene, pyrazolylene, thiazolylene, thiadiazolylene, isothiazolylene, triazinylene, tetrazinylene, triazolylene, tetrazolylene, furazanylene, pyridinylene, pyrazinylene, benzofuranylene, and benzothiophenylene.

8. A polymer material obtained by a polymerization reaction using the diamine monomer compound of claim 1.

9. A polyamic acid represented by Chemical Formula 9 below obtained by a polymerization reaction between the diamine monomer compound of claim 1 and a tetracarboxylic acid represented by Chemical Formula 7 below or dianhydride represented by Chemical Formula 8 below:

[Chemical Formula 7]

[Chemical Formula 8]

[Chemical Formula 9]

in Chemical Formulas 7 to 9, $L_1$ is each independently O, S or Se;

$L_2$ is each independently (C6-C30)arylene or (C6-C30)heteroarylene, wherein heteroarylene includes at least one heteroatom selected from the group consisting of =B—, =N—, —O—, —S—, —P(=O)—, —Si— and P, and arylene and heteroarylene may be further substituted with at least one selected from the group consisting of (C1-C30)alkyl, halo(C1-C30)alkyl, halogen, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C1-C30)alkyl-substituted (C3-C30)heteroaryl, (C6-C30)aryl-substituted (C3-C30)heteroaryl, mono- or di(C1-C30)alkylamino, mono- or di(C6-C30)arylamino, tri(C1-C30)alkylsilyl, di(C1-C30)alkyl(C6-C30)arylsilyl, tri(C6-C30)arylsilyl, nitro and hydroxy;

A is (C3-C30)cycloalkyl, (C3-C30)heterocycloalkyl, (C6-C30)aryl or (C3-C30)heteroaryl, wherein heterocycloalkyl and heteroaryl each independently include at least one heteroatom selected from the group consisting of =B—, =N—, —O—, —S—, —P(=O)—, —Si— and P;

n is an integer of 5 to 100,000; and $X_1$ is halogen.

10. The polyamic acid of claim 9, wherein A is selected from the following structures:

11. The polyamic acid of claim 9, is obtained by a polymerization reaction using 10 to 100 parts by weight of the tetracarboxylic acid or dianhydride based on 100 parts by weight of the diamine monomer compound.

12. A polyimide obtained by a cyclization reaction of the polyamic acid of claim 9.

* * * * *

UNITED STATES PATENT AND TRADEMARK OFFICE
CERTIFICATE OF CORRECTION

PATENT NO. : 9,783,639 B2
APPLICATION NO. : 14/958010
DATED : October 10, 2017
INVENTOR(S) : Chang-Sik Ha et al.

Page 1 of 2

It is certified that error appears in the above-identified patent and that said Letters Patent is hereby corrected as shown below:

In the Specification

Column 8, Lines 45 – 53, delete "  "

and insert --  --

Column 10, Lines 6 – 14, delete "  "

Signed and Sealed this
Thirteenth Day of March, 2018

Andrei Iancu
*Director of the United States Patent and Trademark Office*

CERTIFICATE OF CORRECTION (continued)
U.S. Pat. No. 9,783,639 B2 and insert --  --